(12) United States Patent
Nelson

(10) Patent No.: US 11,678,993 B2
(45) Date of Patent: Jun. 20, 2023

(54) HUMERAL HEAD TRIAL WITH FLEXURE

(71) Applicant: Howmedica Osteonics Corp., Mahwah, NJ (US)

(72) Inventor: Andrew J. Nelson, New City, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 170 days.

(21) Appl. No.: 17/178,340

(22) Filed: Feb. 18, 2021

(65) Prior Publication Data

US 2021/0251768 A1 Aug. 19, 2021

Related U.S. Application Data

(60) Provisional application No. 62/978,398, filed on Feb. 19, 2020.

(51) Int. Cl.
*A61F 2/46* (2006.01)
*A61F 2/40* (2006.01)

(52) U.S. Cl.
CPC .......... *A61F 2/4014* (2013.01); *A61F 2/4684* (2013.01); *A61F 2002/4029* (2013.01)

(58) Field of Classification Search
CPC ............ A61F 2/4684; A61F 2002/4029; A61F 2002/30614; A61F 2002/30607; A61F 2002/30616; A61F 2002/3069
See application file for complete search history.

(56) References Cited

U.S. PATENT DOCUMENTS

| | | | |
|---|---|---|---|
| 6,673,114 B2 | 1/2004 | Hartdegen et al. | |
| 6,776,799 B2 | 8/2004 | Ball et al. | |
| 7,431,736 B2 | 10/2008 | Maroney et al. | |
| 7,632,283 B2 | 12/2009 | Heldreth | |
| 8,663,334 B2 | 3/2014 | Viscardi et al. | |
| 8,753,402 B2 | 6/2014 | Winslow et al. | |
| 8,858,641 B2 | 10/2014 | Viscardi et al. | |
| 8,906,102 B2 | 12/2014 | Viscardi et al. | |
| 8,945,138 B2 | 2/2015 | Klotz et al. | |
| 9,216,090 B2 | 12/2015 | Metcalfe | |
| 9,510,952 B2 | 12/2016 | Muir et al. | |
| 9,597,191 B2 | 3/2017 | Muir et al. | |
| 9,681,954 B2 | 6/2017 | Klotz | |

(Continued)

FOREIGN PATENT DOCUMENTS

| CA | 2347042 A1 | 3/2001 |
|---|---|---|
| EP | 2668930 A1 | 12/2013 |

OTHER PUBLICATIONS

Kolken et al., Auxetic mechanical metamaterials, RSC Advances, Jan. 2017, pp. 5111-5129, The Royal Society of Chemistry.

*Primary Examiner* — Alvin J Stewart
(74) *Attorney, Agent, or Firm* — Lerner David LLP

(57) ABSTRACT

Disclosed herein is a humeral head trial, a system for humeral trialing, and a method for removing a humeral head trial from a humeral stem. The humeral head trial may include a first portion, a second portion, and a post extending from the second portion. The first portion may define a convex articular surface with a movable surface substantially flush with the convex articular surface. The post may define a first length in a first configuration and a second length in a second configuration. The first length may be greater than the second length. The post may change from the first configuration to the second configuration by moving the movable surface with respect to the convex articular surface.

21 Claims, 8 Drawing Sheets

(56) References Cited

U.S. PATENT DOCUMENTS

| | | |
|---|---|---|
| 10,034,759 B2 | 7/2018 | Deransart et al. |
| 10,245,164 B2 | 4/2019 | Muir et al. |
| 10,390,972 B2 | 8/2019 | Rao |
| 10,588,752 B2 | 3/2020 | Winslow et al. |
| 2017/0281355 A1 | 10/2017 | Winslow et al. |
| 2018/0133018 A1 | 5/2018 | Winslow |
| 2018/0168815 A1 | 6/2018 | Muir et al. |

HUMERAL HEAD TRIAL WITH FLEXURE

CROSS-REFERENCE TO RELATED APPLICATIONS

The present application claims the benefit of the filing of U.S. Provisional Patent Application No. 62/978,398, filed Feb. 19, 2020, the disclosure of which is hereby incorporated herein by reference.

FIELD OF THE DISCLOSURE

The present disclosure relates generally to an apparatus and a method of sizing implants, and in particular relates to a trial and a method for using a trial for implant sizing.

BACKGROUND OF THE DISCLOSURE

In an orthopedic joint replacement procedure, a surgeon may use a trial that is representative of a prosthesis or implant to assess the placement and size of the prosthesis or implant prior to implantation. In some instances, the trial preferably is secured firmly on an implant to allow for articulation of a patient's joint with the trial secured to the implant in order to evaluate the trial, and thus the prosthesis or implant represented by the trial. However, firmly securing a trial to the implant may prevent ready attachment and detachment of the trial to and from the implant. Further, removing a firmly secured trial from an implant may require significant extraction forces which may be transferred to the implant during removal.

Various extractors may be used for pulling, manipulating and/or inserting the trial of an implant into the implant site. Such extractors may also be used for removing a trial of an implant, or the implant itself, from cemented or cementless applications. Current solutions often implement osteotomy or other cutting methods to remove trials. In such solutions there is a risk of damaging the bone periphery, the soft tissues and the bone implant site. The connection between the extractor and the implant in many such systems may be achieved through cumbersome and time consuming means that do not effectively and easily engage the extractor and quickly remove the implant. For example, many extractors are threaded directly onto the trial.

Thus, an improved trial and a method for implant sizing using a trial are desired.

BRIEF SUMMARY OF THE DISCLOSURE

In certain embodiments, the present disclosure relates generally to a humeral head trial. In other embodiments, the present disclosure relates to a system for humeral trialing. In still other embodiments, the present disclosure relates to a method for removing a humeral head trial from a humeral stem.

In an aspect of the present disclosure, a humeral head trial is provided. In accordance with this aspect, the humeral head trial may include a first portion, a second portion, and a post extending from the second portion. The first portion may define a convex articular surface. The convex articular surface may include a movable surface substantially flush with the convex articular surface. The second portion may define a flat surface. The post may define a first length in a first configuration and a second length in a second configuration. The first length may be greater than the second length. The post may change from the first configuration to the second configuration by moving the movable surface with respect to the convex articular surface.

Continuing in accordance with this aspect, the humeral head trial may be adapted to be secured to a prosthetic humeral stem when the post is in an opening of the humeral stem in the first configuration. The first length may be equal to or larger than an opening length of the opening such that the post forms an interference fit with the opening in the first configuration. The humeral head trial may be adapted to be detached from the humeral stem by moving the post from the opening in the second configuration. The second lengthn may be smaller than the opening length such that the post may be removed from the opening in the second configuration. The post may be adapted to be removed from the opening in the second configuration without contacting sidewalls of the opening. The first portion may be adapted to articulate with a glenoid, a glenoid implant, or a glenoid trial through a range of shoulder motion when the humeral head trial is secured to the humeral stem.

Continuing in accordance with this aspect, the post may include first and second legs such that a distance between the first and second legs measured parallel to the second portion may be greater in the first configuration than in the second configuration. The movable surface may be connected to the first leg such that moving the movable surface in a first direction with respect to the convex articular surface may move the first leg toward the second leg. The first direction may be toward an interior of the convex articular surface. The first direction may be tangential to the convex articular surface. The movable surface may be connected to the first leg by a connection member. The connection member may include a flexible element to bias the post toward the first configuration in the absence of applied force. The flexible element may include a pair of flexure walls that may be substantially parallel in the absence of applied force. The flexure walls may be curved toward an interior of the convex articular surface. The moveable surface may include first and second moveable surfaces. The first moveable surface may be directly connected to the first leg. The second moveable surface may be directly connected to the second leg. The first and second moveable surfaces may be located on opposite sides of the convex articular surface.

Continuing in accordance with this aspect, the humeral head trial may be adapted to be secured to a humeral stem when the post is in an opening of the humeral stem in the first configuration such that a locking member on the post is secured in a corresponding recess in the opening. The first portion, the movable surface, the second portion, and the post may be integrally formed.

In a further aspect of the present disclosure, a humeral trialing system is provided. A humeral trialing system according to this aspect, may include a humeral head trial and a humeral stem. The humeral head trial may include a first portion, a second portion, and a post extending from the second portion. The first portion may define a convex articular surface. The convex articular surface may include a movable surface substantially flush with the convex articular surface. The second portion may define a flat surface. The post may define a first length in a first configuration and a second length in a second configuration. The first length may be greater than the second length. The post may change from the first configuration to the second configuration by moving the movable surface. The humeral stem may have an opening. The humeral head trial may be adapted to be secured to the humeral stem when the post is in the opening of the humeral stem in the first configuration. The first length may be the equal to or larger than an opening length such that the post forms an interference fit with the opening in the first configuration.

Continuing in accordance with this aspect, the humeral trialing system may include a glenoid implant or glenoid trial. The first portion may be adapted to articulate with the glenoid implant or glenoid trial through a range of shoulder motion when the humeral head trial is secured to the humeral stem.

Continuing in accordance with this aspect, the humeral head trial may be adapted to be detached from the humeral stem by removing the post from the opening in the second configuration. The second length may be smaller than the opening length such that the post can be removed from the opening in the second configuration.

In a further aspect of the present disclosure, a method of removing a humeral head trial from a prosthetic humeral stem is provided. A post of the humeral head trial may be secured within an opening of the humeral stem. A method according to this aspect may include the steps of moving a movable surface of a convex articular surface of the humeral head trial to transition from a first configuration to a second configuration and removing the humeral implant trial from the humeral stem while the post in the second configuration. The movable surface may be substantially flush with the convex articular surface in the first configuration. The post may extend from a second portion of the humeral head trial. The post may define a first length in the first configuration and a second length in the second configuration. The first length may be larger than the second length. The second length may be smaller than an opening length.

Continuing in accordance with this aspect, the step of removing the humeral head trial from the humeral stem may include removing the post from the opening without contacting side walls of the opening.

BRIEF DESCRIPTION OF THE DRAWINGS

A more complete appreciation of the subject matter of the present disclosure and the various advantages thereof may be realized by reference to the following detailed description, in which reference is made to the following accompanying drawings.

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "implant trial" and "trial" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, the term "distal" means toward the human body and/or away from the operator, and the term "proximal" means away from the human body and/or towards the operator.

Figure 1:
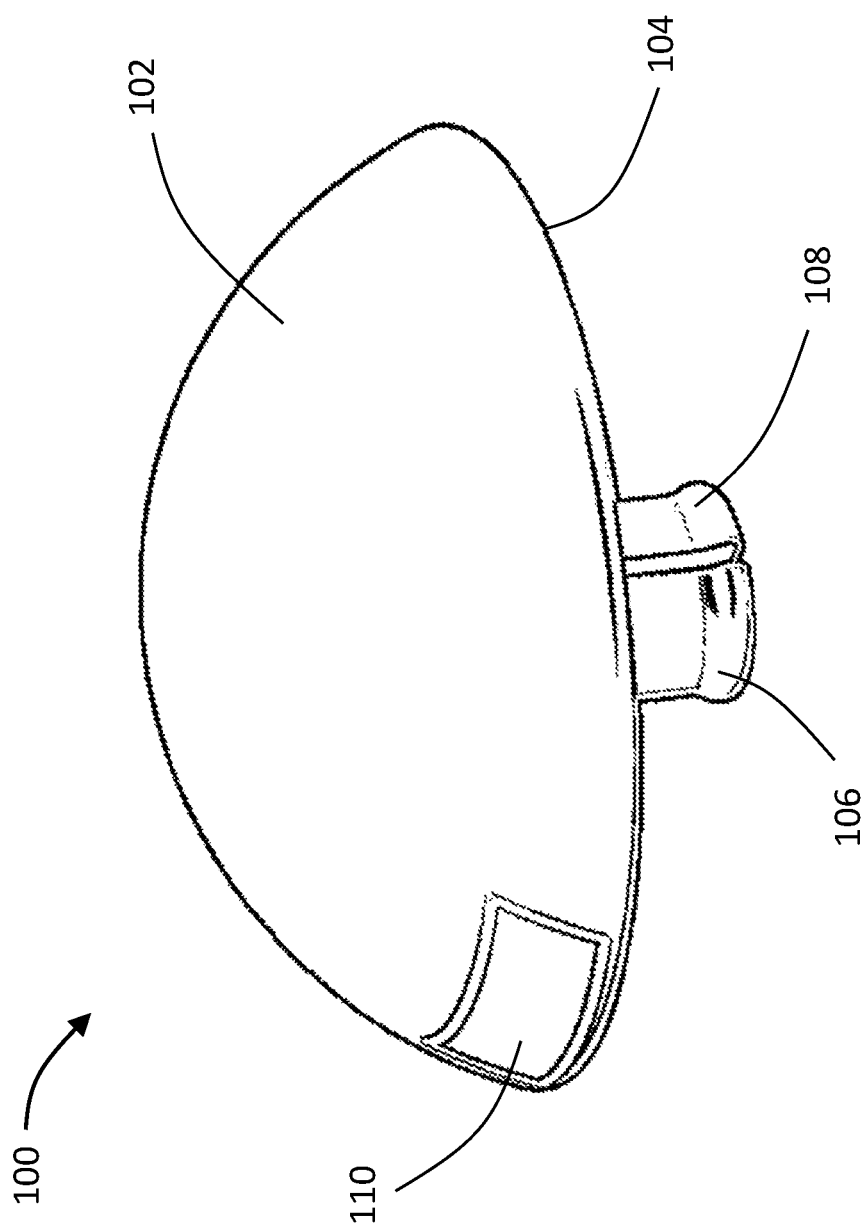
FIG. 1 is a top perspective view of a humeral head trial according to an embodiment of the present disclosure.

Referring now to FIG. 1, there is shown a humeral head trial 100 according to an embodiment of the present disclosure. Humeral head trial 100 includes a convex articular surface 102 and a flat surface 104. Articular surface 102 is configured to articulate with a glenoid, a glenoid implant or a glenoid trial through a range of shoulder motion when humeral head trial 100 is attached to a humeral stem. A post having a first leg 106 and a second leg 108 extends from flat surface 104. A movable surface 110 is located on articular surface 102. Movable surface 110 lies flush with articular surface 102 and blends with the contours of the articular surface to facilitate articulation of humeral head trial 100. The shape—i.e., curvature, and position of the movable surface is configured to blend with articular surface 102 as best shown in FIG. 1. While movable surface 110 is shown as a rectangular-shaped surface in this embodiment, movable surface 110 can be shaped differently in other embodiments. While movable surface 110 is located adjacent to flat surface 104 of humeral head trial 104 in this embodiment, movable surface 110 can be located anywhere along articular surface 102 in other embodiments. Humeral head trial 100 has a size and shape that generally corresponds with, or is representative of, a prosthetic humeral head intended for permanent implantation into a prosthetic humeral stem that has been implanted in the humerus.

Figure 2:
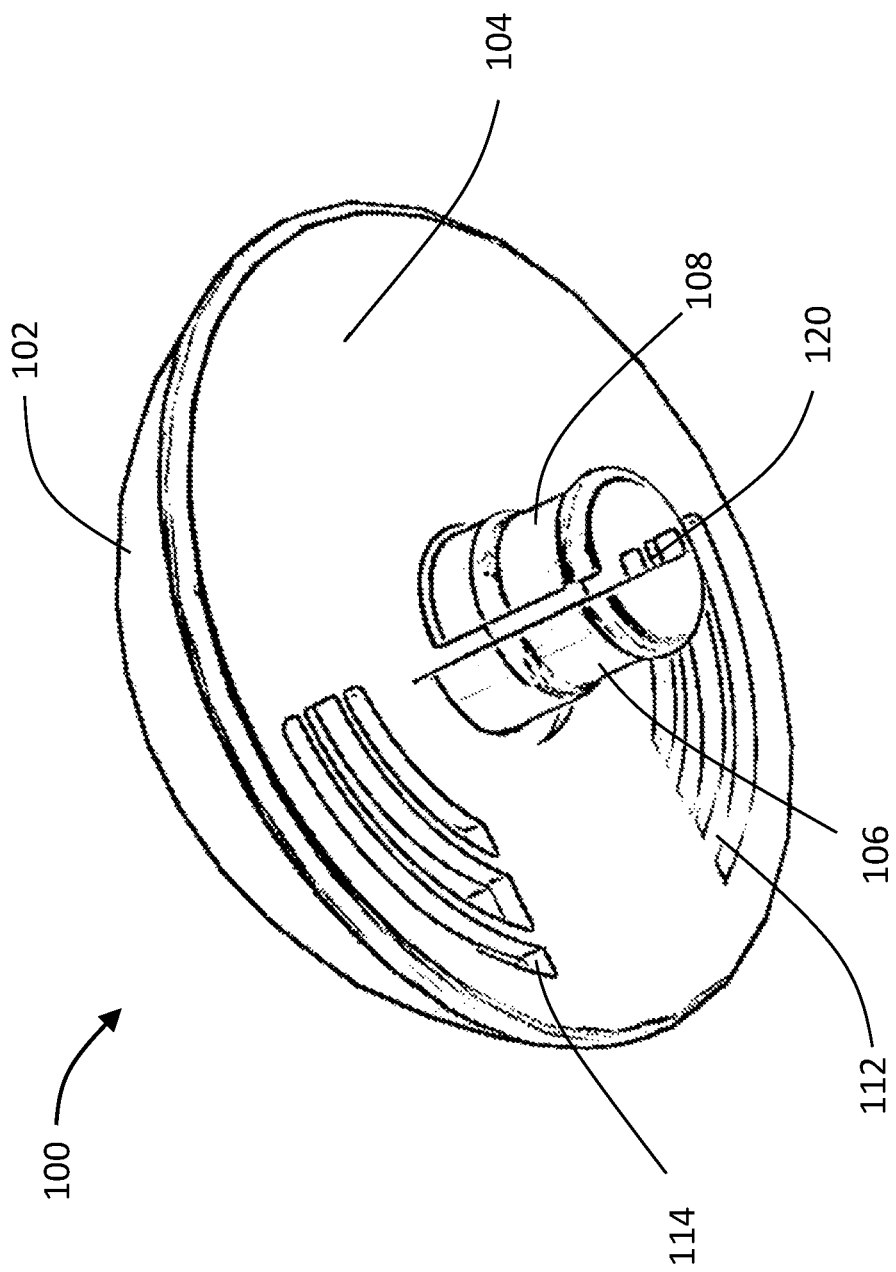
FIG. 2 is a bottom perspective view of the humeral head trial of FIG. 1.
Figure 3:
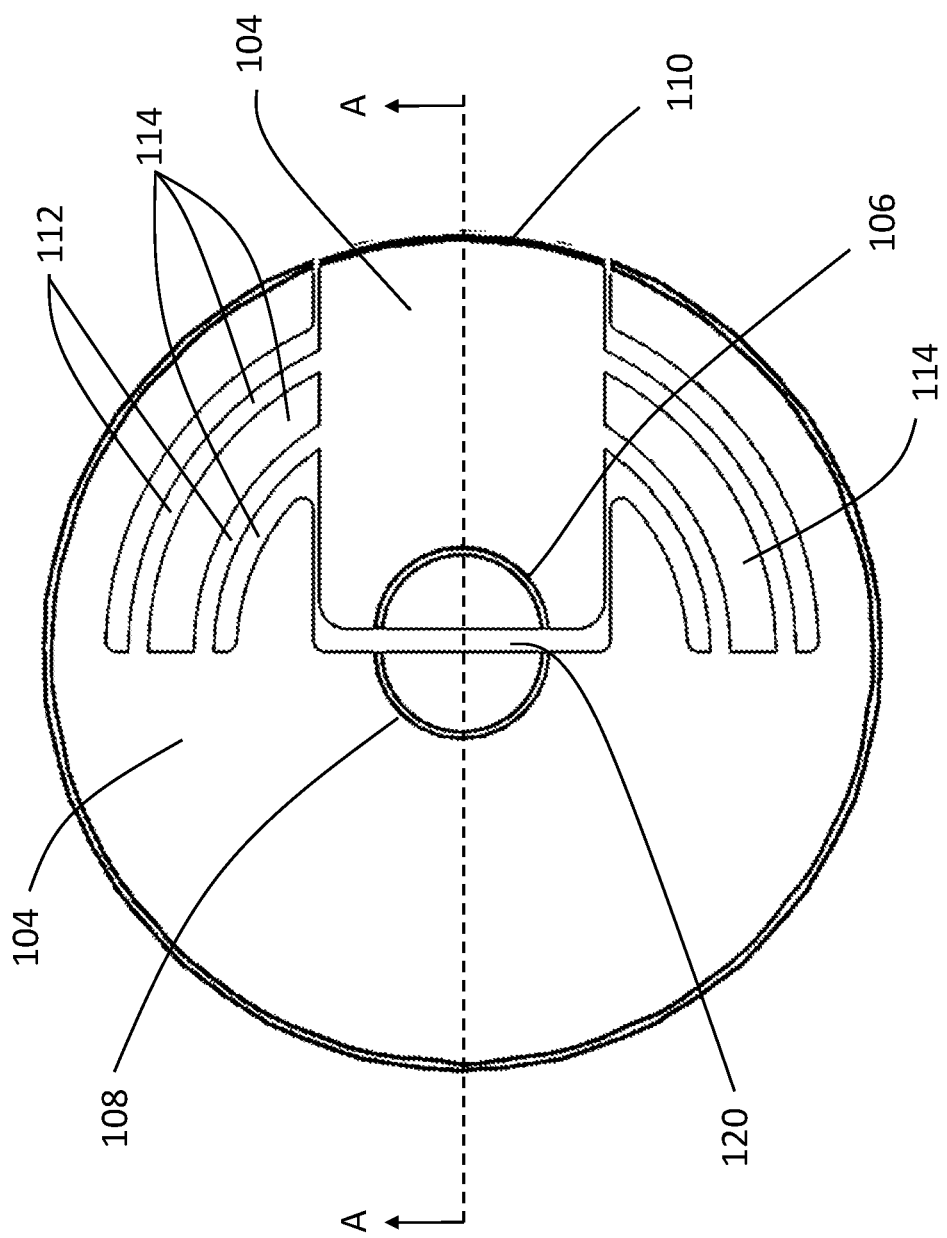
FIG. 3 is a bottom view of the humeral head trial of FIG. 1.
Figure 4:
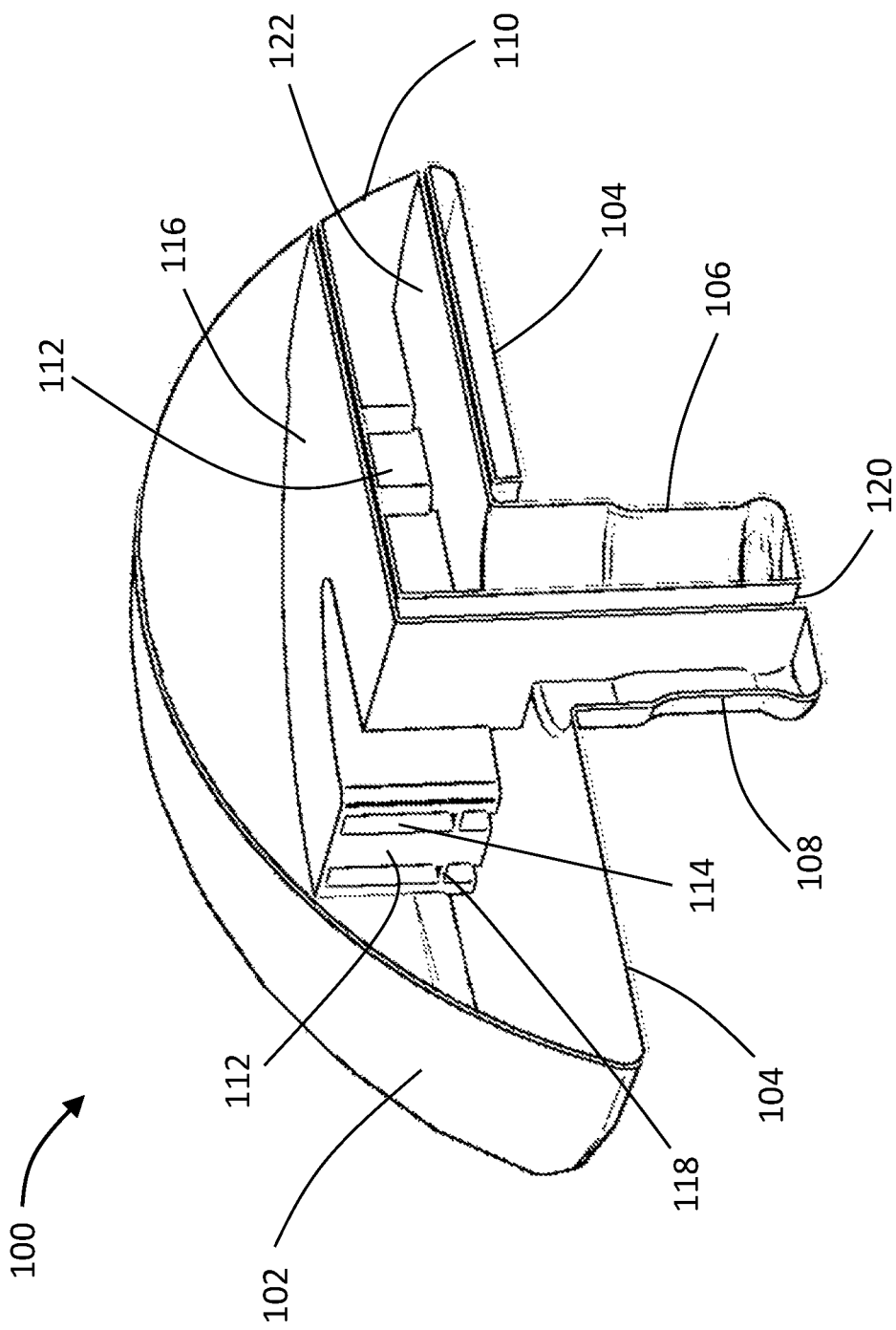
FIG. 4 is a side cross-sectional perspective view of the humeral head trial of FIG. 1 taken along line A-A of FIG. 3.

FIG. 2 shows a bottom perspective view of humeral head trial 100. A gap 120 separates first leg 106 and second leg 108 of the post. A series of flexible walls 112 separated by slots 114 are visible on flat surface 104. FIG. 3 shows a bottom view of humeral head trial 100 illustrating the layout of flexible walls 112 and slots 114. Flexible walls 112 and slots 114 extend semicircularly around movable surface 110. A perspective view of a cross-section through line A-A of FIG. 3 is shown in FIG. 4 illustrating the details of movable surface 110. Movable surface 110 is connected to first leg 106 via an arm 122. A flexible structure 116 containing flexible walls 112 (and defining slots 114) is configured to bias movable surface 110 against articular surface 102 as more fully explained below.

Flexible structure 116 includes three flexible walls 112 with two slots 114 between them as shown in FIG. 4. Ribs 118 are provided on slots 112 to reinforce the biasing effect of flexible structure 116. The flexible wall may be between about 0.020" and about 0.050" thick (0.5 cm to 0.12 cm) and have a height of between about 0.25" and about 0.5" (0.63 cm to 1.27 cm) in this embodiment. Depending on the materials of the humeral head trial, these dimensions may be varied to produce the desired biasing force. While three flexible walls and two slots extending semicircularly are shown in this embodiment, other embodiment can have one or more walls and slots arranged in a linear, non-linear, or any other layout in other embodiments. While a flexible structure with flexible walls and slots is shown in this embodiment, other flexible structures such as springs, elastic elements, etc. can be used in other embodiments to bias the movable surface toward the articular surface.

Figure 5B:
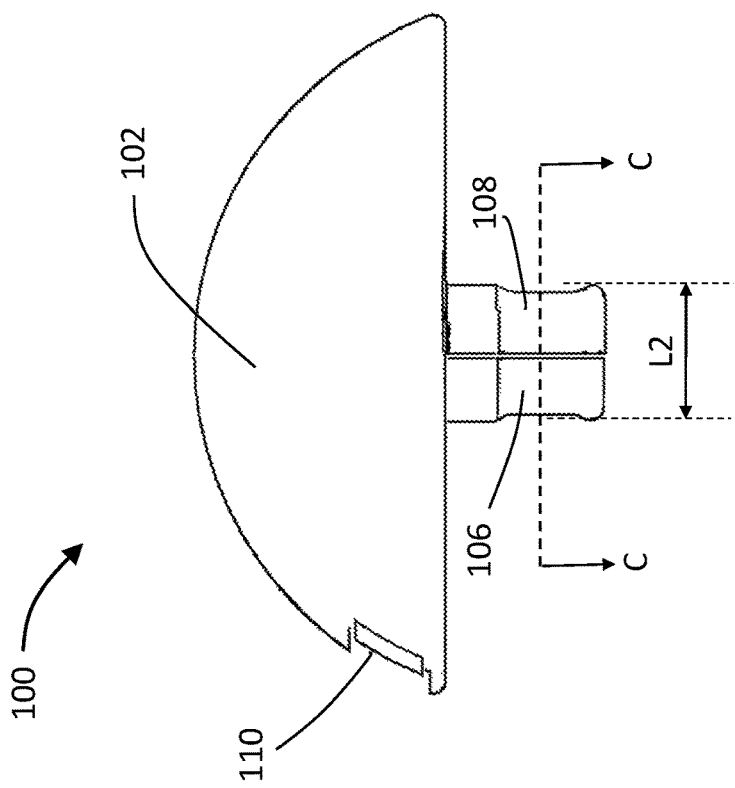
FIG. 5B is a side view of the humeral head trial of FIG. 1 in a second configuration.
Figure 5A:
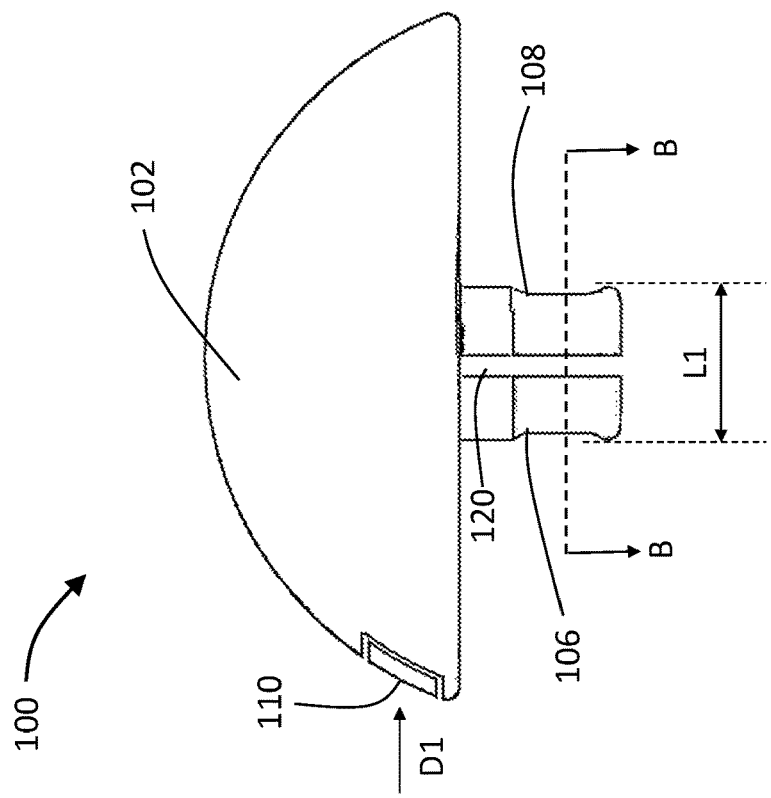
FIG. 5A is a side view of the humeral head trial of FIG. 1 in a first configuration.
Figure 6B:
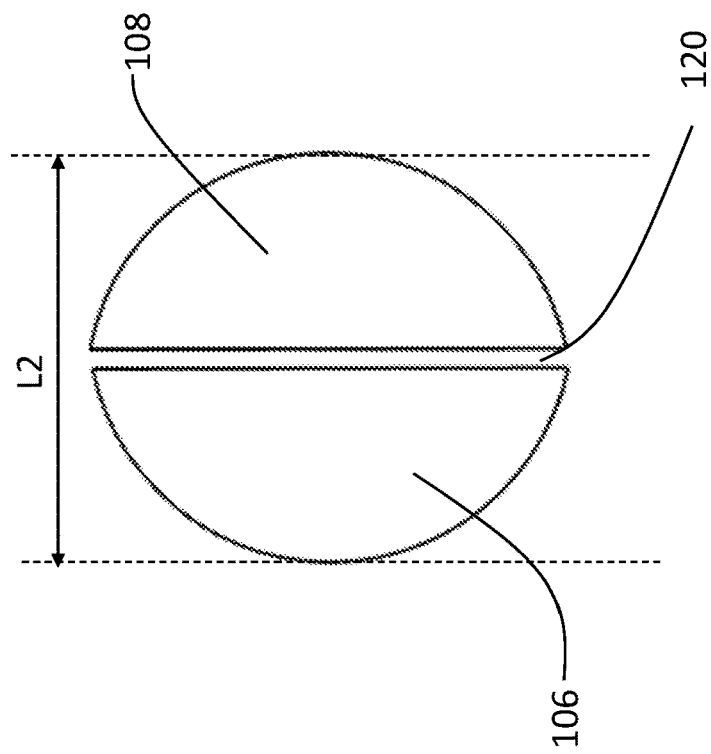
FIG. 6B is a cross-sectional view of the humeral head trial of FIG. 5B along line C-C.
Figure 6A:
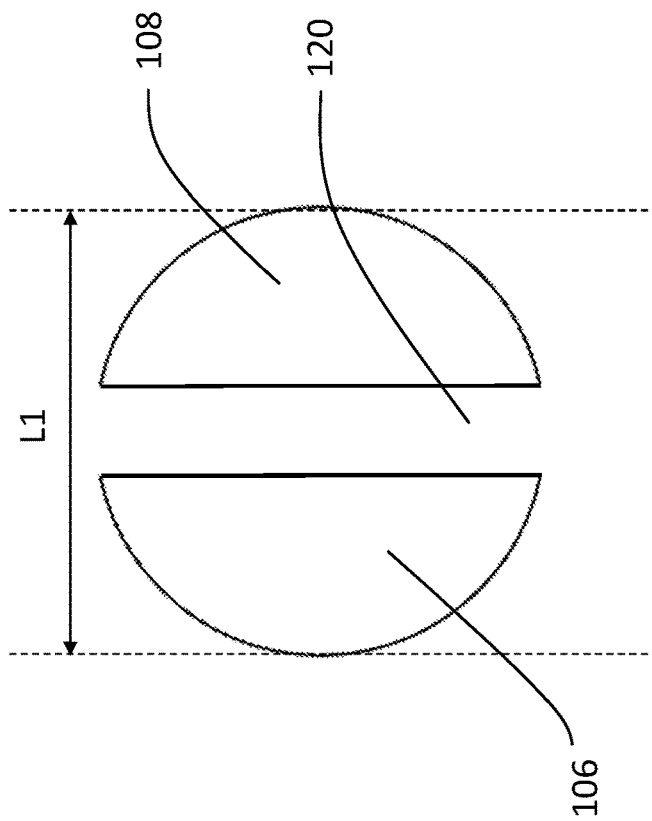
FIG. 6A is a cross-sectional view of the humeral head trial of FIG. 5A along line B-B.

FIGS. 5A, 5B, 6A and 6B illustrate the operation of movable surface 110. As shown in FIG. 5A, gap 120 and legs 106, 108 define a first length L1 when humeral head trial 100 is in a rest condition, for example in the absence of applied force. FIG. 6A illustrates a cross-section of the post at line B-B of FIG. 5A. When movable surface 110 is pushed toward an interior of humeral head trial 100 along a direction D1 as shown in FIG. 5A, leg 106, which is attached to movable surface 110 via arm 122, moves toward leg 108 as best shown in FIG. 5B. Consequently, a second length L2 in a flexed condition as illustrated in FIG. 5B is less than L1 because gap 120 is reduced. As shown in FIG. 6B, a cross-section of the post in the flexed condition taken at line C-C of FIG. 5B is less than the cross-section of the post in the rest condition as shown in FIG. 6A. When the application of force is removed from movable surface 110, flexible structure 116 ensures that movable surface is moved back to the exterior of humeral head trial 100 to restore gap 120 to the rest condition shown in FIGS. 5A and 6A. Thus, an operator can readily control a length or cross-section of the post by manipulating the movable surface. While the movable surface shown in the present embodiment is moved toward the interior of the humeral head trial to change gap distance, the movable surface can be moved tangentially in any direction with respect to the articular surface to adjust the gap distance in other embodiments.

Figure 7:
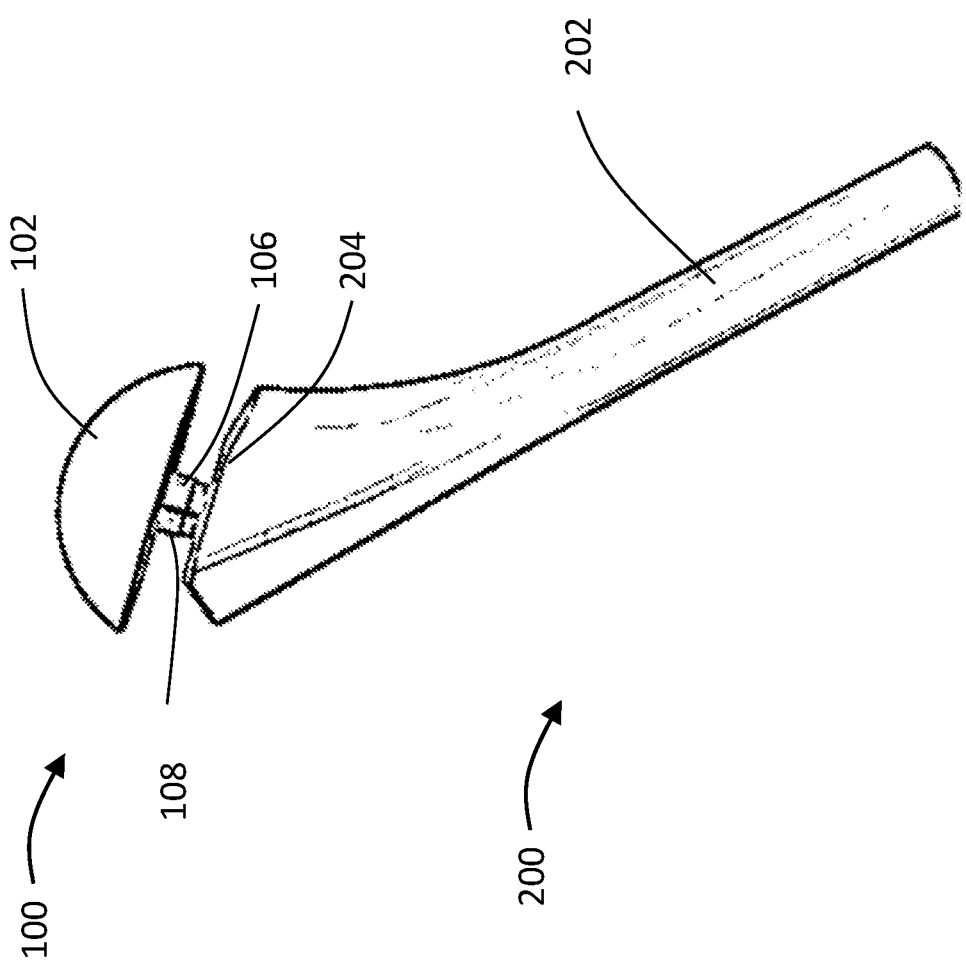
FIG. 7 is perspective view of the humeral head trial of FIG. 1 on a humeral stem according to another embodiment of the present disclosure.
Figure 8:
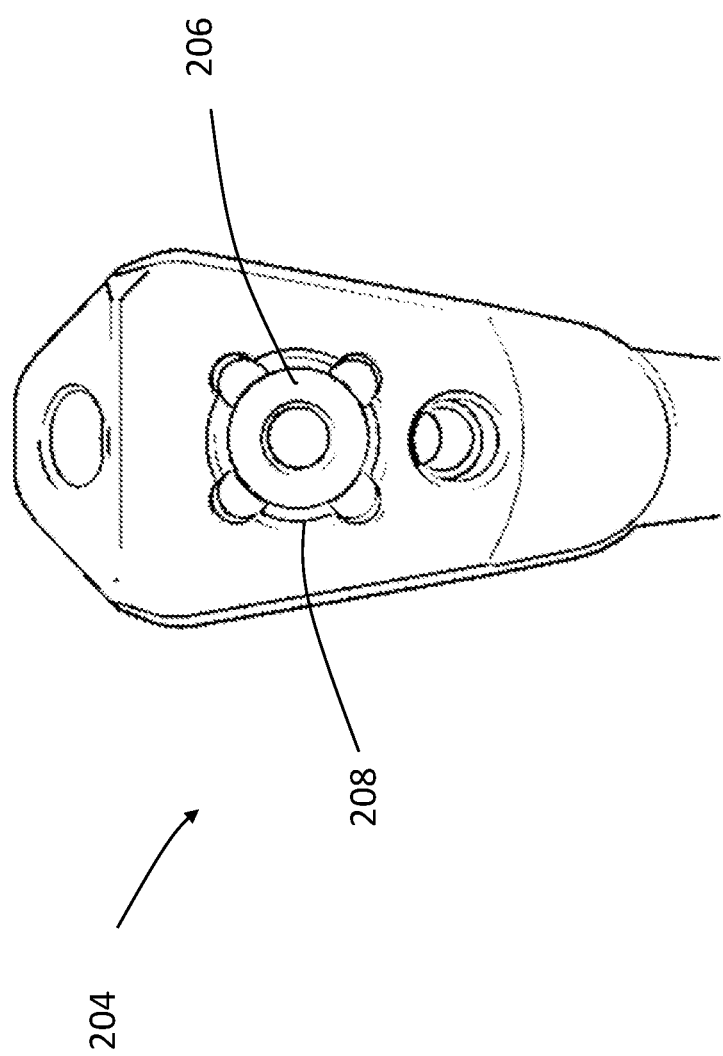
FIG. 8 is a top view of the humeral stem of FIG. 7.

Referring to FIG. 7, there is shown humeral head trial 100 attached to a prosthetic humeral stem 200 according to an embodiment of the present disclosure. Humeral stem 200 includes a body 202 which may be inserted into a patient's humerus, for example along the intramedullary canal after the native humeral head has been removed. A proximal face 204 includes an opening 206 with sidewalls 208 to receive legs 106, 108 of the post of humeral head trial 100.

In another embodiment of the present disclosure, a method of attaching and removing humeral head trial 100 from prosthetic humeral stem 200 is described. Attaching and removing humeral head trial 100 from prosthetic humeral stem 200 may be performed to minimize or eliminate any forces that may be imparted to the implanted prosthetic humeral stem during these steps. An operator can couple humeral head trial 100 to prosthetic humeral stem 200 by pressing movable surface 110 along direction D1 and inserting the post into opening 206 of humeral stem 200 while the post has the smaller length L2. A cross-section and/or length of opening 206 is less than the cross-section or length L1 of the post in the rest condition (FIGS. 5A and 6A), but equal to or greater than the cross-section or length L2 of the post in the flexed condition (FIGS. 5B and 6B). Thus, the post can be placed into opening 206 without imparting any force (or imparting only small amounts of force) to prosthetic humeral stem 200 while the post is in the flexed condition. Upon releasing the force on movable surface 110, the gap 120 is restored back to the rest condition, so that the post returns to length L1, causing legs 106, 108 to contact sidewalls 208 and form a friction or interference fit to firmly secure humeral head trial 100 to prosthetic humeral stem 200. With the humeral head trial 100 secured to the prosthetic humeral stem 200, the size and shape of the humeral head trial may be evaluated. For example, the shoulder may be taken through a range of motion, with the humeral head trial 100 articulating against a native or prosthetic glenoid component of the shoulder, to determine if the humeral head trial provides an acceptable range of motion. Similarly, tightness, gaps, or other resulting features of the shoulder joint may be evaluated while the humeral head trial 100 is coupled to the prosthetic humeral stem 200 to determine if the size and shape of the humeral head trial is acceptable.

After trialing, the humeral head trial 100 may be removed, either to allow for implantation of a prosthetic humeral head that corresponds to the acceptable trial, or to couple a differently sized and/or shaped humeral head trial for another trialing step. Applying force on movable surface 110 along direction D1 will move the post of the humeral head trial 10 to the flexed condition, and allow an operator to remove humeral head trial 100 from prosthetic humeral stem 200 without contacting sidewalls 208 and thereby imparting no removal forces (or minimal removal forces) on the prosthetic humeral stem. Thus, an operator can conveniently trial various humeral head trials 100 by securing and removing the trials without disturbing the placement of the humeral stem. It should be understood that, if significant forces were imparted to the prosthetic humeral stem 200 upon coupling of the humeral head trial 100 to the prosthetic humeral stem (or upon removal of the humeral head trial from the prosthetic humeral stem), the prosthetic humeral stem may be pushed into or pulled out of the native humerus, or otherwise become re-oriented. If the prosthetic humeral stem 200 changed positions and/or orientations before or after trialing, the results of the trialing may not accurately reflect the appropriateness of the corresponding prosthetic humeral head that is later coupled to the prosthetic humeral stem.

Various other modifications can be made to the embodiments described above. For example, legs 106, 108 can include tapered ends wherein a length of the tapered ends is less than length L1 to allow an operator to place the tapered ends into opening 206 without manipulating the movable surface. Once the tapered ends are placed in the opening, the operator can gently push down on the humeral head trial to secure it to the prosthetic humeral stem 200. Removal can be performed as described above by depressing the movable surface. In another embodiment, a plurality of movable surfaces can be provided to facilitate improved access for an operator to transition the humeral head trial from the rest condition to the flexed condition. For example, a first movable surface on one side of the articular surface can be connected to the first leg, and a second movable surface on an opposite second side of the articular surface can be connected to the second leg to allow easier access to manipulate both legs of the humeral head trial. In another embodiment, one or both legs of the humeral head trial can include a projection that corresponds to a recess in opening of the humeral stem whereby the movable surface can manipulate the projection to engage and disengage with the recess to allow for attachment and detachment of the humeral head trial from the humeral stem, respectively.

While a humeral head trial in conjunction with a humeral stem are described in the embodiments above, the present disclosure can be used for any other trial such as a femoral implant trial, a tibial implant trial, etc. Implant trials of the present disclosure may be, but are not limited to, being made of any polymer such as polyetheretherketone ("PEEK"), polyarlyetherketones ("PAEK"), ultra-high molecular weight polyethylene ("UHMWPE"), metals such as titanium, stainless steel, aluminum, or other suitable material (e.g., ceramic) that is biocompatible and possess sufficient strength and rigidity. Implant trials can be made using an additive manufacturing process. The trial can be 3d printed such that the flexible structure, posts and movable surface form a monolithic component. In other words, despite leg 106 and moveable surface 110 being moveable relative to leg 108 and articulating surface 102, the humeral head trial 100 may nonetheless be formed as a unitary or monolithic component.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A humeral head trial comprising:
   a first portion defining a convex articular surface, the convex articular surface including a movable surface substantially flush with the convex articular surface;
   a second portion defining a flat surface, and
   a post extending from the second portion, the post defining a first length in a first configuration and a second length in a second configuration, the first length being greater than the second length,
   wherein the post is configured to transition from the first configuration to the second configuration upon movement of the movable surface with respect to the convex articular surface.

2. The humeral head trial of claim 1, wherein the humeral head trial is adapted to be secured to a prosthetic humeral stem when the post is in an opening of the prosthetic humeral stem in the first configuration, the first length being equal to or larger than an opening length of the opening such that the post forms an interference fit with the opening in the first configuration.

3. The humeral head trial of claim 2, wherein the humeral head trial is adapted to be detached from the humeral stem by removing the post from the opening in the second configuration, the second length being smaller than the opening length such that the post can be removed from the opening in the second configuration.

4. The humeral head trial of claim 3, wherein the post is adapted to be removed from the opening in the second configuration without contacting sidewalls of the opening.

5. The humeral head trial of claim 2, wherein the first portion is adapted to articulate with a glenoid, a glenoid implant, or a glenoid trial through a range of shoulder motion when the humeral head trial is secured to the humeral stem.

6. The humeral head trial of claim 1, wherein the post includes first and second legs such that a distance between the first and second legs measured parallel to the second portion is greater in the first configuration than in the second configuration.

7. The humeral head trial of claim 6, wherein the movable surface is connected to the first leg such that the first leg is configured to move toward the second leg upon movement of the movable surface in a first direction with respect to the convex articular surface.

8. The humeral head trial of claim 7, wherein the first direction is toward an interior of the convex articular surface.

9. The humeral head trial of claim 7, wherein the first direction is tangential to the convex articular surface.

10. The humeral head trial of claim 7, wherein the movable surface is connected to the first leg by a connection member, the connection member including a flexible element to bias the post toward the first configuration in the absence of applied force.

11. The humeral head trial of claim 10, wherein the flexible element includes a pair of flexure walls that are substantially parallel in the absence of applied force, the flexure walls being curved toward an interior of the convex articular surface.

12. The humeral head trial of claim 6, wherein the moveable surface includes first and second moveable surfaces.

13. The humeral head trial of claim 12, wherein the first moveable surface is directly connected to the first leg, and the second moveable surface is directly connected to the second leg.

14. The humeral head trial of claim 13, wherein the first and second moveable surfaces are located on opposite sides of the convex articular surface.

15. The humeral head trial of claim 1, wherein the humeral head trial is adapted to be secured to a prosthetic humeral stem when the post is in an opening of the prosthetic humeral stem in the first configuration such that a locking member on the post is secured in a corresponding recess in the opening.

16. The humeral head trial of claim 1, wherein the first portion, the movable surface, the second portion, and the post are integrally formed.

17. A humeral trialing system comprising:
   a humeral head trial including a first portion defining a convex articular surface, the convex articular surface including a movable surface substantially flush with the convex articular surface, a second portion defining a flat surface, a post extending from the second portion, the post defining a first length in a first configuration and a second length in a second configuration, the first length being larger than the second length, the post is configured to transition from the first configuration to the second configuration upon movement of the movable surface; and
   a prosthetic humeral stem having an opening,
   wherein the humeral head trial is adapted to be secured to the humeral stem when the post is in the opening of the humeral stem in the first configuration, the first length being the equal to or larger than an opening length such that the post forms an interference fit with the opening in the first configuration.

18. The humeral trialing system of claim 17, further including a glenoid implant or glenoid trial, wherein the first portion is adapted to articulate with the glenoid implant or glenoid trial through a range of shoulder motion when the humeral head trial is secured to the humeral stem.

19. The humeral trial system of claim 17, wherein the humeral head trial is adapted to be detached from the humeral stem by removing the post from the opening in the second configuration, the second length being smaller than the opening length such that the post can be removed from the opening in the second configuration.

20. A method of removing a humeral head trial from a prosthetic humeral stem, a post of the humeral head trial being secured within an opening of the humeral stem, the method comprising:

moving a movable surface of a convex articular surface of the humeral head trial to transition a post from a first configuration to a second configuration, the movable surface being substantially flush with the convex articular surface in the first configuration, the post extending from a second portion of the humeral head trial, the post defining a first length in the first configuration and a second length in the second configuration, the first length being larger than the second length, the second length being smaller than an opening length; and removing the humeral head trial from the humeral stem while the post is in the second configuration.

21. The method of claim 20, wherein removing the humeral head trial from the humeral stem includes removing the post from the opening without contacting side walls of the opening.

\* \* \* \* \*